United States Patent [19]

Scheinberg

[11] Patent Number: 4,487,780

[45] Date of Patent: Dec. 11, 1984

[54] METHOD OF TREATMENT OF RHEUMATOID ARTHRITIS

[76] Inventor: Israel H. Scheinberg, 5447 Palisades Ave., Bronx, N.Y. 10471

[21] Appl. No.: 346,208

[22] Filed: Feb. 5, 1982

Related U.S. Application Data

[60] Division of Ser. No. 076,652, Sep. 18, 1979, Pat. No. 4,315,028, which is a continuation-in-part of Ser. No. 926,688, Jul. 21, 1978, abandoned.

[51] Int. Cl.$^3$ ................... A61K 31/30; A61K 31/195
[52] U.S. Cl. ..................................... 424/294; 424/319
[58] Field of Search ................................ 424/319, 294

[56] References Cited

U.S. PATENT DOCUMENTS

| | | | |
|---|---|---|---|
| 3,466,312 | 9/1969 | Ercoli | 260/440 |
| 3,591,686 | 7/1971 | Sheffner et al. | 424/234 |
| 3,792,165 | 2/1974 | McGusty et al. | 424/215 |
| 3,842,108 | 10/1974 | Sutton et al. | 260/430 |
| 4,112,113 | 9/1978 | Hill | 424/275 |
| 4,165,380 | 8/1979 | Hill | 424/290 |

*Primary Examiner*—Stanley J. Friedman
*Attorney, Agent, or Firm*—Blum, Kaplan, Friedman, Silberman & Beran

[57] ABSTRACT

Rheumatoid arthritis is treated with substituted cysteine compounds having a lower toxicity-to-effectiveness ratio than penicillamine. Such compounds are specific alpha-substituted cysteines, beta-monosubstituted cysteines, beta-di-substituted cysteines other than penicillamine, N-acetyl penicillamine and the N-acetyl derivatives of the alpha and beta-substituted compounds mentioned above.

Any of the compounds may be used synergistically in combination with suitable copper compounds or with suitable gold compounds in the treatment of arthritis.

The same compounds are effective in the treatment of cystinuria and heavy metal poisoning. The same compounds as well as penicillamine are effective in combination with copper in the treatment of heavy metal poisoning.

16 Claims, No Drawings

METHOD OF TREATMENT OF RHEUMATOID ARTHRITIS

REFERENCE TO RELATED APPLICATIONS

This is a division, of application Ser. No. 076,652, filed Sept. 18, 1979 now U.S. Pat. No. 4,315,028 which is a continuation-in-part of Ser. No. 926,688, filed July 21, 1978, now abandoned.

BACKGROUND OF THE INVENTION

Rheumatoid arthritis, commonly referred to as RA, is the second most crippling disease in man, ranking immediately behind cardiovascular defects. Until recently no effective treatment for RA has been known. A number of drugs which are moderately effective in the treatment of this disease have been found, examples being D-penicillamine which is $\beta,\beta$-dimethylcysteine and certain compounds of gold, such as gold sodium thiomalate, aurothioglucose and sources of auric or aurous ion.

Of these compounds, the most promising is the recently discovered penicillamine, a natural metabolite of penicillin. Unfortunately, not all patients respond to this medication; also, it carries with it considerable toxicity so that it can, in fact, be lethal. Another difficulty is that, penicillamine is slow-acting so that generally it requires 8 to 12 weeks before it can be determined whether the patient is responding and whether the dosage needs adjusting. D-penicillamine usually produces a decrease in the titer of rheumatoid factor, an index of its specific therapeutic efficacy for this human disease. There are no genuine animal models of rheumatoid arthritis.

At the present time, most rheumatologists treat moderately severe RA that has not responded to salicylates with either a gold compound or D-penicillamine. Penicillamine is also used initially in some patients with severe RA, and those in whom rheumatoid lung disease, vasculitis, amyloidosis, Felty's syndrome or rheumatoid nodulosis complicate the clinical picture.

Publications on the use of D-penicillamine make it clear that the dosage employed in the past for treatment of RA has frequently been too high; it is now generally agreed that a dosage of 1.5 g/day is the maximum required. It still has not been determined how long D-penicillamine therapy in RA should be continued, some rheumatologists taking the position that the drug should be continued indefinitely if it is well tolerated while others attempt to reduce the daily maintenance dose gradually in order to determine the minimum quantity of drug necessary for sustaining remission of the disease.

As is clear from the above, D-penicillamine, while for some RA patients the drug of choice at the present time, presents major difficulties, both with respect to toxicity and to the method of use. It is also frustrating that the mechanism by which the compound acts therapeutically is not understood, this lack of understanding having made it difficult to use this compound as a base from which to explore in the search for compounds having a higher therapeutic efficacy, this efficacy being defined as the ratio of the dose causing toxicosis to that required for therapeutic effectiveness. One clue is at hand, namely, that the efficacy of the compound D-penicillamine is linked to the presence of a sulfhydryl group in the molecule. The naturally occurring amino acid cysteine itself also has a sulfhydryl group in the molecule but is ineffective in the treatment of RA, because it dimerizes to form cystine in vivo, and is metabolized by amino acid oxidases and cysteine desulfhydrase to a much greater degree than penicillamine. The dimer, cystine, excreted in the urine in excessive amounts in a hereditary disorder, cystinuria, forms kidney stones in quantity such that they may be lethal, since the dimer is relatively insoluble while cysteine itself is quite soluble. Further, it is evident that the equilibrium between the monomer and the dimer is far over on the side of the dimer, since, otherwise, in patients with cystinuria, dissociation of cystine to the soluble monomer would prevent the formation of cystine stones. D-penicillamine proved to be effective in the treatment of cystinuria because the asymmetrical dimer that is formed—a combination of one molecule of cysteine and one molecule of D-penicillamine—possesses a relatively high solubility so that it is readily excreted from the body.

While D-penicillamine has been more widely used than either the L-isomer or the racemic mixture, it is recognized that any of the three forms may have unique value in specific instances, so that the term "penicillamine" as used herein will be taken to include both isomers and the racemic mixture.

As aforenoted, the mechanism by which penicillamine causes remission of RA is unknown. Just as unknown is the cause of RA itself. However, one reason why penicillamine was investigated was the fact that penicillin which is generally well tolerated by the body, is metabolized in part to penicillamine so that it is apparent that the body can tolerate penicillamine also even if in smaller quantity. I have found that certain closely related compounds which are not natural metabolites of penicillin are at least as effective as penicillamine for the treatment of RA as well as of cystinuria and heavy-metal poisoning.

SUMMARY OF THE INVENTION

Cysteine derivatives useful in the treatment of RA and having lower toxicity and greater therapeutic effect than penicillamine are alpha-substituted cysteines, beta-monosubstituted cysteines, beta-disubstituted cysteines other than penicillamine, alpha-substituted cysteines which are either mono- or di-substituted in the beta position, and N-acetyl derivatives of each of the above which are hereinafter more fully set forth.

The specific sulfhydryl compounds useful in the treatment in RA are members of the following 5 groups:

1. Cysteine derivatives in which one of the beta hydrogens is replaced by Cl, $CH_3$, $C_2H_5$, $CH_2OH$ or $CH_2CH_2OH$;

2. Cysteine derivatives in which both of the beta hydrogens are replaced by one of the following pairs of substituents:

| | |
|---|---|
| chloro, | chloro, |
| methyl, | chloro, |
| ethyl, | chloro, |
| methyl, | ethyl, |
| ethyl, | ethyl, |
| hydroxymethyl, | hydroxymethyl, |
| hydroxyethyl, | hydroxylethyl, |
| hydroxymethyl, | hydroxyethyl, |
| methyl, | hydroxymethyl, |
| methyl, | hydroxyethyl, |
| ethyl, | hydroxymethyl, |
| ethyl, | hydroxyethyl, |
| chloro, | hydroxymethyl, and |
| chloro, | hydroxyethyl; |

3. Cysteine derivatives in which the alpha hydrogen is replaced by Cl, $CH_3$, $C_2H_5$, $CH_2OH$ or $CH_2CH_2OH$;

4. Cysteine derivatives in which the alpha hydrogen and one or both of the beta hydrogens are each replaced by Cl, $CH_3$, $C_2H_5$, $CH_2OH$ or $CH_2CH_2OH$ in any of the possible combinations; and 5. The N-acetyl derivatives of any of the compounds in the groups 1 to 4.

The preferred compounds, on the basis of the therapeutic efficacy, are $\beta$-methylcysteine, $\alpha$-methylcysteine and $\alpha$-methyl, $\beta$-methylcysteine. Cysteine and derivatives thereof will hereinafter be referred to generally as sulfhydryls or sulfhydryl compounds.

A further discovery which I have made is that the efficacy of all of the above compounds is increased in the treatment of RA when combined or complexed with copper or gold and in the treatment of heavy metal poisoning when combined or complexed with copper. Still further, the effectiveness of penicillamine is increased in the treatment of RA when used in combination with or complexed with copper or gold and in heavy metal poisoning when combined with or complexed with copper. Penicillamine, $\beta$-methyl cysteine and cysteine itself are preferred sulfhydryls for use in combination with or complexed with copper. The gold compound used is preferably water-soluble, examples being chlorauric acid, gold sodium thiomalate and aurothioglucose.

The medication, where a sulfhydryl is used alone is administered initially to a 150 lb patient suffering from RA in a single dose of 100 mg amounting to 1.5 mg/day per kilogram of the patient's weight and is increased by 25 mg/day at 2-3 week intervals up to 500 mg/day and then by 50 mg/day at 8-12 week intervals to a maximum of 1500 mg/day or until RA symptoms are alleviated. The dose is administered in capsule or tablet form or as a suitably formulated solution subcutaneously, intramuscularly or intravenously. If the medication is well tolerated the rate of increase at the end of each interval can be 50 mg/day.

Where any of the above sulfhydryls or penicillamine is administered with gold either in combination or complexed therewith for treatment of RA, the initial daily dosage in 2 doses per day is such that the gold content thereof is 10 mg. The form of the dose is as a solid in a capsule or tablet form or as a suitably formulated solution for injection as above. The dosage is increased as needed by 10 mg/day (of gold) at intervals of 2-4 weeks to 100 mg/day and then by increments of 20 mg/day at intervals of 8-12 weeks to a maximum of 200 mg/day. Preferably, the sulfhydryl content of the combinations with gold is at least equal to that of the gold by weight and may be up to 4 times the weight of the gold.

Where any of the above sulfhydryls or penicillamine is administered with copper either in combination or complexed therewith for treatment of RA the initial daily dosage is preferably 25 mg/day of the combination in 1 or 2 doses/day, the copper content of the dosage being about 7.5 mg with the remainder a sulfhydryl, the preferred sulfhydryl being penicillamine. The dosage is increased in increments of 25 mg/day at intervals of 2-3 weeks until a dosage of 150 mg/day is reached after which the dosage is increased at intervals of 8-12 weeks in increments of 50 mg/day to a maximum of 400 mg/day.

It will be noted that the dosage of penicillamine when used in combination with either copper or gold is much smaller than when administered without these metals.

A method of treating cystinuria is to administer an effective amount of any of the types of sulfhydryl compounds in the above 5 groups, $\beta$-monomethylcysteine being preferred because of its relatively low toxicity and the solubility of the mixed dimer with cysteine. The initial dosage is 100 mg/day and can be increased by steps of 100 mg/day at intervals of 2 weeks to a maximum of 1.50 g/day. The dosage may be administered orally as a solid in capsule or tablet form or a solution or by injection when suitably formulated for injection as above and should be administered 1 or 2 times per day.

A method of removing heavy metals such as mercury, lead, cadmium, bismuth, vanadium and plutonium from the body is to administer either orally or by injection a sulfhydryl from one of the above 5 groups either as such or combined with copper. The combination of penicillamine with copper is particularly effective. A complex of copper with a sulfhydryl is denoted as RSCu where RSH is a sulfhydryl of one of the above groups, penicillamine or cysteine; cysteine, $\beta$-monomethylcysteine and penicillamine are the preferred sulfhydryl compounds for use with copper. The method of using such RSCu compounds is restricted to removal of those heavy metals having a high enough association constant with the sulfhydryls to displace copper from the complex and having the capacity to form a soluble compound with the sulfhydryl. The method is particularly effective for removal of mercury, an exceedingly toxic element. The initial dosage of the complex of a sulfhydryl with copper is 200 mg repeated at 8-hour intervals, as capsules or tablets or by injection as a suitably formulated solution. The dosage is increased by steps of 200 to 400 mg depending on the amount of mercury ingested and the response of the patient, the maximum daily dosage being 2.00 g. The preferred combination are copper penicillamine, copper cysteine and copper $\beta$-methyl cysteine.

Where the cystinuria patient is to be treated with a sulfhydryl, any of the sulfhydryls in the above 5 groups may be administered as a capsule or tablet or as a suitably formulated solution by injection, the preferred compounds being $\alpha$-methyl cysteine and $\beta$-methyl cysteine. The initial dosage is 1.00 g/day this being administered in 3 divided doses, the dosage being increased daily in steps of 0.5 g/day until a maximum of 3.00 g/day is reached.

Accordingly, an object of the present invention is a method of treating rheumatoid arthritis with selected cysteine derivatives.

A further object of the present invention is a method of treating rheumatoid arthritis with combinations of cysteine, and selected cysteine derivatives, including penicillamine with gold compounds and with copper compounds.

Still another object of the present invention is a method of eliminating from the body heavy metals present in excess quantity by administration of specific sulfhydryls, either as such or complexed with copper. Still further, penicillamine complexed with copper can be used for this purpose.

A significant object of the present invention is a method of treating cystinuria by administration of specific cysteine derivatives other than penicillamine.

Yet another object of the present invention are compositions of selected sulfhydryl compounds with copper or with gold, such compositions being effective for treatment of RA and compositions of selected sulfhydryls with copper, such compositions being effective in the treatment of heavy metal poisoning.

An important object of the present invention is a method of minimizing side effects of the chemotherapy of rheumatoid arthritis and cystinuria and elimination of toxic metals from the body.

Still other objects and advantages of the invention will in part be obvious and will in part be apparent from the specification.

The invention accordingly comprises the several steps and the relation of one or more of such steps with respect to each of the others, and the composition possessing the features, properties, and the relation of constituents, which are exemplified in the following detailed disclosure, and the scope of the invention will be indicated in the claims.

DESCRIPTION OF THE PREFERRED EMBODIMENTS

D-penicillamine, which is moderately effective in the treatment of rheumatoid arthritis, is a metabolite of penicillin; it can also be prepared synthetically. Prior to its use for the treatment of RA, it was found effective in Wilson's disease, in cystinuria and in the removal of toxic metals such as lead from the body. It has long been approved by the Food & Drug Administration as safe and effective for Wilson's disease and cystinuria. In Wilson's disease, ingested copper is not properly excreted. Apparently, in the removal of copper by treatment with penicillamine, chelates are formed with involvement of the SH group and the amino group attached to the alpha carbon. Cystinuria is a disorder in which the amount of cystine in the urine exceeds the solubility of this amino acid, with the result that ultimately fatal stones form in the kidney. Penicillamine forms an asymmetrical disulfide with cysteine of which one-half is the penicillamine molecule and the other half is the cysteine molecule. Although its use in the treatment of rheumatoid arthritis has recently been approved by the Food & Drug Administration, it has not as yet been approved for treatment of lead or mercury poisoning largely because of its toxicity which includes allergic reactions and direct toxicity to skin, kidneys, lung, bone marrow, and neuromuscular system.

Penicillamine differs from the natural amino acid cysteine only in that the two β-hydrogen atoms are replaced by methyl groups. It is almost certain that it is the presence of these two methyl groups which keeps the molecule from forming penicillamine disulfide to the extent that cysteine dimerizes to cystine, so that an appreciable fraction of penicillamine—in contrast to cysteine—circulates in the body with a free SH group. As aforenoted, an asymmetrical disulfide is formed with cysteine. Moreover, it seems probable that the effect of penicillamine on rheumatoid arthritis is also related to the free SH group.

A further point with respect to the biochemistry of penicillamine is that sulfhydryl amino acids are metabolized by desulfhydrases and by amino oxidases. Tests have shown that these enzymes react only very slowly with the penicillamine isomers. However, cysteine is very rapidly attacked by both enzymes which also accounts for the low concentration of cysteine in the blood and for its lack of effectiveness in the removal of toxic metals from the blood.

Since there are two asymmetric carbon atoms in the β-methyl-substituted cysteine, there are four diastereoisomers. The rate of attack on each of the isomers by D-amino acid oxidase and L-amino oxidase has been measured and, interestingly, the rate of attack is not nearly so high as the rate of attack on cysteine itself. Accordingly, it can be seen that substitution of from 1 to 3 of the hydrogen atoms on the alpha and beta carbons of cysteine with substituents of small size offers the possibility of modifying the rate of attack by amino acid oxidases and cysteine desulfhydrases, as well as the solubility, the toxicity and the effect of the compound on RA. A further enhancement of the therapeutic efficacy of appropriately chosen substituents is afforded by replacement of one of the hydrogens on the amino group with an acetyl group.

A first group of compounds useful in the treatment of RA consists of those cysteine derivatives in which one of the beta hydrogens is replaced by a chlorine atom or a methyl, ethyl, hydroxymethyl or hydroxyethyl group. A second group of cysteine derivatives useful in the treatment of RA is that consisting of the beta-disubstituted cysteines in which the substituents consist of one of the following pairs:

| | |
|---|---|
| chloro, | chloro, |
| methyl, | chloro, |
| ethyl, | chloro, |
| methyl, | ethyl, |
| ethyl, | ethyl, |
| hydroxymethyl, | hydroxymethyl, |
| hydroxyethyl, | hydroxyethyl, |
| hydroxymethyl, | hydroxyethyl, |
| methyl, | hydroxymethyl, |
| methyl, | hydroxyethyl, |
| ethyl, | hydroxymethyl, |
| ethyl, | hydroxyethyl, |
| chloro, | hydroxymethyl, and |
| chloro, | hydroxyethyl. |

A third group of compounds useful in the treatment of RA is the alpha-substituted cysteines, where the single substituent is a chlorine atom or a methyl, ethyl, hydroxymethyl or hydroxyethyl group.

A fourth group of cysteine derivatives useful in the treatment of RA is that in which the alpha carbon is substituted as in the third group and the beta carbon is substituted as in either the first group or the second group. In other words, the alpha carbon is substituted and the beta carbon is either mono- or di-substituted.

A fifth group of cysteine derivatives particularly useful in the treatment of RA is obtained by forming the N-acetyl derivatives of any of the compounds in the first four groups.

Methods of synthesis of all of the compounds listed in the above five groups are well known to those skilled in the art. The compounds are stable and can be dried for administration in a capsule or as a tablet. They can also be formulated for administration subcutaneously, intramuscularly or intravenously.

The side effects attendant upon the use of the above compounds can be minimized through the use of two or more of the above compounds in combination, each compound being used in a dosage smaller than would be the case were it used alone. Accordingly, combinations of compounds in any of the above five groups may be used in the treatment of RA as well as combinations of said compounds with penicillamine.

In the Examples which follow, the dosages cited are appropriate for an individual weighing 68 kg (150 lb). Where the patient's weight differs substantially from this figure, the dosages should be adjusted appropriately. Moreover, all dosages, including periodic increases, must be subject to the clinician's judgement with respect to the entire patient's situation so that even the dosages to be presented as maxima can under appropriate circumstances be exceeded.

The symptoms and signs of RA are well known, these being pain in the joints, swelling of the joints, redness and heat in the joints and loss of mobility. During treatment with sulfhydryl compounds, the patient is monitored to determine the clinical response as assessed by symptomatic change and by objective change. The objective change is noted in the mobility, redness, swelling and heat of the joints. The objective assessment of the state of the patient's rheumatoid activity is further evaluated by measurement of the concentration of the rheumatoid factor in the blood, by the white blood count and the differential count, by the erythrocyte sedimentation rate, and by measurement of the fluorescent anti-nuclear antibody. In addition, the progression of the arthritis—or its remission—may on occasion be estimated by suitable X-ray studies. Here again, the frequency of the tests and the variety thereof are a matter for the clinician's judgment.

Possible toxic effects to be noted include early rash, fever, leukopenia and thrombocytopenia, all of the foregoing usually occurring as allergic manifestations in the first two to four weeks of treatment. Late toxicity is manifested most importantly as suppression of bone marrow, or by toxic effects to the kidneys, lungs or skin.

With respect to the examples of treatment for various conditions as presented herein, the examples are not to be considered as presenting fixed and unalterable dosage schedules. Actually, treatment schedule must be established by the physician on the basis of all relevant clinical information.

Treatment of a patient suffering from RA with sulfhydryl is illustrated in the following examples.

EXAMPLE 1

A patient showing the symptoms of rheumatoid arthritis is treated with $\beta$-methylcysteine in a capsule containing the powdered solids. The initial dosage is 100 mg/day in a single dose. This amounts to 1.5 mg/kg/day, the patient weighing approximately 68 kg. The patient's condition is monitored with respect to the aforenoted objective changes and laboratory tests.

At the end of two weeks, the degree of remission being considered minor, the dosage is increased by 25 mg/day, the dosage increase being repeated at 2 week intervals in steps of 25 mg/day up to 500 mg/day, after which the dosage is increased in steps of 50 mg/day at intervals of 8 weeks to a maximum of 1000 mg/day to provide for further remission, the patient's condition being monitored before each increase in dosage both for degree of improvement and side effects.

EXAMPLE 2

To a patient suffering with RA is administered each day a tablet including 25 mg of $\alpha$-methyl cysteine and 25 mg of $\alpha$-chloro, $\beta$-hydroxyethyl cysteine, the patient weighing 68 kg. The dosage is continued for 3 weeks, at which time, the degree of remission and side effects, on examination of the patient being minimal, the dosage of each compound is increased by 25 mg/day to induce further remission. The procedure is repeated, the increases being made at intervals of 3 weeks and in steps of 50 mg/day until a maximum of 400 mg/day is reached after which the increases are made at intervals of 12 weeks and in increments of 100 mg/day to achieve further remission until a maximum of 1200 mg/day is reached, the patient being monitored before each increase in the dosage for the degree of remission and for tolerance of the medication.

In general in the treatment of RA with a single sulfhydryl compound as disclosed herein, the initial dosage is 100 mg/day (for a 68 kg patient), increased at intervals of 2–3 weeks, depending on the response and tolerance of the patient, by steps of 50 mg/day until a dosage of 500 mg/day is reached after which the increments are at 100 mg/day at 8–12 week intervals until a dosage of 1500 mg/day is reached.

In all of the examples given herein the dosages are for a 68 kg individual, the quantities for patients of different weight being adjusted so that the dosage is proportional to the weight. It should also be noted that where tablets or capsules or solutions are to be administered, fillers, solubilizing agents and buffers well known to those in the art may be present, although not specifically mentioned herein. Furthermore, where gold or copper compounds are to be combined with sulfhydryl compounds, the metal compounds must be pharmaceutically acceptable.

As aforenoted, gold compounds have been found to be effective in the treatment of RA, examples of such gold compounds being gold sodium thiomalate, aurothioglucose and ionic gold. Colloidal gold can also be used. Combinations of gold from the above sources with sulfhydryls as listed above present advantages with respect to effectiveness in the treatment of RA and decrease in toxicity. The combination with penicillamine is particularly noteworthy, a principal advantage provided by this combination being the enhanced therapeutic efficacy in comparison with either of the components when used alone. Evidence is available that the greater efficacy stems from the formation of a complex between the gold atom and penicillamine. It appears likely that the combination of a sulfhydryl with gold is a complex or chelate, but the present invention is not to be considered as dependent on the formation of a complex or chelate. The same comment applies to the complexes of copper with sulfhydryls to be described below. The gold complexes are readily made by combining a weak solution of chlorauric acid with the selected sulfhydryl. These comments apply to any of the aforenoted substituted cysteines as well as to penicillamine and to cysteine itself. The diminished incidence of toxicity from the combination of gold with penicillamine in comparison to gold alone, is consistent with the fact that penicillamine is effective in the treatment of gold toxicosis in man.

In establishing the dosage for treatment of RA with a combination of gold and a sulfhydryl compound, it is necessary to take into account the gold content of the dose. A suitable initial daily dosage is 10 mg (0.15 mg/kg) of gold itself and the method of establishing the composition of the medication is illustrated in the following examples.

EXAMPLE 3

The rheumatoid arthritis patient is to be treated with a combination of penicillamine and gold, the latter being in the form of gold sodium thiomalate monohydrate. Capsules are prepared, each capsule containing 9.9 mg of the gold compound and 10 mg of penicillamine, the patient being administered two capsules per day for an initial period of 3 weeks with monitoring at weekly intervals of the patient's condition and for retention of gold.

The degree of remission being insufficient, the dosage is increased by two capsules per day at intervals of 3 weeks until a dosage of 100 mg/day of gold is reached after which the dosage is increased by 4 capsules/day at intervals of 10 weeks until a maximum dosage of 200 mg/day of gold is reached to provide further remission, the patient's condition being monitored with respect to the same observations as described in connection with treatment with a sulfhydryl alone as well as with respect to retention of the gold and its known toxic effects, particularly on skin, bone marrow and kidneys.

EXAMPLE 4

A solution containing 10.4 mg of anhydrous chlorauric acid and 20 mg of α-methyl cysteine per ml is dried to a powder and made up into capsules each containing either 5.0 mg of gold or 20 mg of gold in combination with the sulfhydryl compound. Treatment of an RA patient is started with administration of the 2 of the 5 mg capsules/day, one in the morning and one in the evening and continued for 3 weeks at which time the patient is monitored both clinically and objectively to determine the degree of remission. The degree being inadequate, the dosage is increased in steps of 10 mg of gold per day at intervals of 4 weeks until a dosage of 100 mg of gold/day is reached after which the dosage is increased at intervals of 11 weeks by increments of 20 mg/day until a dosage of 200 mg/day of gold is reached in order to provide further remission.

More generally, the dosage of gold in any suitable gold compound is increased initially at two to four week intervals in increments of 10 mg/day to a maximum of 100 mg/day as indicated by assessment of the patient's rheumatoid activity. After the dosage has reached 100 mg/day, should further increase in dosage appear to be necessary, the dosage is increased by 20 mg/day at eight to twelve week intervals until a maximum dosage of 200 mg/day is reached. Assessment of the patient's condition is based on the same indications as described in the case of treatment with sulfhydryls alone.

Where the gold compound and the sulfhydryl are administered in combination but not necessarily as a complex or chelate, a preferred mixture as the initial dose consists of 5 mg of the sulfhydryl and a quantity of gold compound such that it contains 5 mg of gold, but the weight of sulfhydryl may be up to twice that of the gold. The mixture is to be taken twice daily. As aforenoted, gold sodium thiomalate, gold thioglucose and ionic gold are suitable sources of gold. Then, as the treatment proceeds, the quantities of the mixture are increased by the amounts of gold as given for the gold chelate and at the same intervals. Either or both of the gold compound and the sulfhydryl may be administered in capsule or tablet form or by injection, either independently or together. In general, where the two materials are combined in solution a complex of the gold with the sulfhydryl will form.

The course of the treatment may be monitored as described above. In addition, the 24-hour urinary output of gold may be determined. This measurement will assess the net effect of gastrointestinal absorption (in the case of oral administration of the drug) and on the metabolism or retention of the metal or compound in the body.

Copper is also effective in the treatment of RA when used in combination with any of the aforenoted sulfhydryls, including penicillamine, the combination with penicillamine being preferred. As is the case with gold, the copper may be provided in the form of a complex with said sulfhydryls. Copper may also be provided as a separate compound in a mixture with any of the sulfhydryls. Cupric ion reacts fairly rapidly with sulfhydryls such as penicillamine to form a complex which in aqueous solution is red-violet in color, the wave length of the absorption maximum being at 520 nanometers. The gram-atomic extinction coefficient at the maximum is 947. It is believed that at least a part of the copper is univalent in the complex.

P. Birker and H. Freeman have shown that when $Cl^-$ is present, soluble copper compounds react with penicillamine (Pen) to produce the anion $[Cu_8{}^I Cu_6{}^{II} Pen_{12}Cl]^{5-}$, the cation being $Na^+$ or $K^+$ depending on the salt in the solution. The moiety indicated as Pen is doubly charged negatively.

Where sulfhydryls are to be administered in combination with copper for treatment of RA, the dosage for the first 2 to 4 weeks should be such that the initial dose of the complex will contain 5 mg of copper. Then should larger doses appear to be necessary, the increments in dosage at 2 to 4 week intervals will be equal to the initial dosage until the dose is six times the initial dosage after which the increments will be twice the initial dosage at intervals of eight to twelve weeks. The maximum copper dosage should rarely reach or exceed 100 mg/day. Where the complex of copper with a specific sulfhydryl has low solubility as is the case with copper cysteine, it must be administered orally. Where the sulfhydryl (with or without copper or gold) is sufficiently soluble, it can be administered parenterally or orally as a solution for any of the conditions discussed herein. In general the weight ratio of the sulfhydryl to copper will be about 2 to 3.

Where either gold or copper is to be administered for the treatment of RA, the combination of the metal with the sulfhydryl may be in the form of a complex as described in the case of copper-penicillamine, or as a mixture of water-soluble metal compound and sulfhydryl or both. In general, it is desirable that, in the preparation of a complex, an excess of at least 30 molar percent of the sulfhydryl be present since oxidation of part of the sulfhydryl may take place in forming the complex. Moreover, should the tolerance of the patient for the metal be lower than for the sulfhydryl, then a combination of the metal chelate with an even greater excess of the sulfhydryl should be administered according to the judgment of the clinician.

Where a sulfhydryl is to be administered in combination with a copper or gold compound, said compound is preferably water-soluble as well as pharmaceutically acceptable. However, a water-insoluble metal compound may be rendered soluble by complexing or chelation with the sulfhydryl and thereby be made effective in the treatment of RA as well as in the treatment of heavy metal poisoning. Moreover, different complexes (or chelates) may be used with each other, such combinations offering the possibility of a higher therapeutic efficacy.

Combination of soluble cupric or cuprous salts with sulfhydryls, and more specifically, with cysteine, beta-monomethylcysteine and penicillamine are of particular value in the treatment of RA. The synergism of D- penicillamine with copper salts in this regard is detailed in the following:

P. E. Lipsky and Morris Ziff. The Effect of D-Penicillamine on Mitogen-Induced Human Lymphocyte Proliferation: Synergistic Inhibition by D-Penicillamine and Copper Salts. Journ. of Immunology, 120: 1006–1013, March 1978.

The above paper is incorporated herein by reference.

In general, it is preferable that the sulfhydryl be present in substantial stoichiometric excess over the copper salts, the ratio of sulfhydryl to copper in mols, being at least 1.3 and up to about 5, the excess sulfhydryl serving to maintain part of the copper in the cuprous state.

The following example illustrates treatment of RA with a combination of copper and penicillamine.

EXAMPLE 5

In preparation for treatment of a patient suffering with rheumatoid arthritis a complex of copper with a sulfhydryl is synthesized as follows:

Cupric acetate is dissolved in water to prepare a solution having a concentration of 10 mg $Cu^{++}$/ml. D-penicillamine is dissolved in 0.05 molar sodium acetate buffer, pH 5.6, containing 2% sodium chloride to give a concentration of 10 mg penicillamine/ml. The copper solution is added to the penicillamine solution in a ratio of 16 ml of copper solution to 50 ml of penicillamine solution. The ratio of penicillamine to copper in moles is 1.3. The solution immediately takes on a red-violet color indicating the formation of the complex. The solution is dried to yield a powder and formed into tablets each containing 10 mg of the combination.

The initial daily dosage of the copper-penicillamine combination is 20 mg in two tablets, one taken in the morning and the other in the evening. This dosage corresponds to 5 mg of copper and 15 mg of penicillamine. The assessment of the clinical response of the patient and the detection of any toxic effect are carried out in the same manner as in patients with RA treated with sulfhydryls alone or with sulfhydryls in combination with gold. Also, the dosage of the compounds is monitored by a determination of the 24-hour urinary output of copper to assess the net effect of gastrointestinal absorption and of the metabolism or retention of the copper or copper compound in the body.

The degree of remission being inadequate, the dosage is increased by steps of 20 mg/day taken at three week intervals until a dose of 200 mg/day is reached after which the increases are 40 mg/day at intervals of 10 weeks in order to achieve further remission until a maximum of 600 mg/day is reached.

It is significant that the quantity of penicillamine administered with copper is far smaller than when penicillamine is administered without copper. The mol ratio of penicillamine to copper preferably lies in the range from 1.3 (as above) to 5, although higher ratios may also be useful depending on the response of the patient.

Copper-sulfhydryl combinations can also be effective when administered as solutions as illustrated by the following example.

EXAMPLE 6

For treatment of an RA patient cupric acetate is dissolved in water to prepare a solution having a concentration of 5 mg $Cu^{++}$/ml. One ml of this copper acetate solution is added with stirring to 4 oz of beef bouillon. To this is added 125 mg of solid penicillamine, as powder; the mixture is stirred until the penicillamine dissolves and is administered orally once per day, on an empty stomach for two weeks. On the last day the patient is examined for clinical changes, specifically with respect to mobility pain, swelling, redness and heat of the joints. Also, the erythrocyte sedimentation rate and concentration of rheumatoid factor in the blood are noted. The results indicating remission to a minor degree, the daily dosage is increased to 8, 12 and then 16 ounces of the solution at one week intervals by administering the 4 ounce quantity of solution, twice, three times and four times daily. Also, the patient is examined as above on the last day of each interval. The degree of remission being insufficient after 4 weeks of treatment, a broth having twice the aforenoted concentrations of copper and penicillamine is prepared and the daily dosage is increased by 4 ounces of the concentrated broth at 4 week intervals to achieve further remission, the patient again being monitored on the last day of each interval as aforenoted. The increases are continued until the daily dosage reaches 40 ounces, this dosage corresponding to a daily intake of 100 mg of copper and 2.5 grams of penicillamine.

As aforenoted, penicillamine is effective in the treatment of cystinuria due to the fact that it forms a mixed disulfide with cysteine, said disulfide having a higher solubility than cystine. However, cysteine derivatives other than penicillamine offer the advantages of higher solubility and different or milder side effects. Accordingly, specific sulfhydryls other than penicillamine also have value in the treatment of cystinuria.

The preferred dosage range for treatment of cystinuria with a sulfhydryl from the aforenoted 5 groups is from about 0.5 to 2.0 grams per day. Treatment starts with administration of 0.5 grams/day, the dosage being increased by about 0.25 grams/day at intervals of one week. The increase is continued until there is no further formation of stones or until maximum dosage of 2.0 g/day is reached, the condition of the patient being monitored radiologically and for cysteine in the urine.

The treatment of cystinuria with sulfhydryl is related to the fact that the rate of dissolution of stones depends upon the solubility of the mixed dimer. Where a combination of sulfhydryls is administered, then two or more mixed dimers with cysteine will be formed so that the rate of dissolution of the stones will not be limited by the solubility of a single mixed dimer such as the mixed dimer of cysteine with penicillamine.

The sulfhydryl compounds useful in the treatment of cystinuria are those listed in the aforenoted five groups. Combinations of the members of these groups with each other and with penicillamine are also useful. Particularly useful, due to solubility characteristics and structural similarity to cysteine are the $\alpha$-methyl and $\beta$-methyl cysteines as illustrated in the following Example.

EXAMPLE 7

A cystinuria patient is treated with capsules each containing 50 mg of $\alpha$-methyl cysteine and 50 mg of $\beta$-methyl cysteine, a dose of one capsule being administered twice daily. The extent of remission being minor, the dosage is increased at intervals of 4 weeks by two capsules/day to provide further remission, the patient being monitored at the end of each interval for the quantity of cysteine as the mixed dimer in the urine.

The daily dosage is increased until a dosage of 2 g/day is reached and then increased by 4 capsules/day at intervals of 4 weeks until a maximum dosage of 3.0 g/day is reached. The treatment is continued until chemical and radiological examination indicate that existing cystine stones are dissolving and no new stones are forming.

The sulfhydryl compounds in the aforenoted 5 groups are effective in removing heavy metals, and particularly mercury and lead from those suffering from heavy metal poisoning. Those heavy metal ions having a high association constant with said sulfhydryls and forming a soluble complex or chelate therewith can be removed from the body by administration of specific sulfhydryls. Heavy metals which can be eliminated in this way, in addition to mercury and lead are, for example, cadmium, bismuth, vanadium and plutonium. The progress of the treatment is monitored by frequent examination of the urine for the metal in question. The procedure is illustrated in the following example.

EXAMPLE 8

A patient suffering from acute mercury poisoning is treated with β-methyl cysteine in tablet form, the patient being given 0.25 g both morning and evening on the first day. The patient is monitored for mercury in the urine and toxic effects. The dosage is increased daily by 0.5 g/day until a maximum of 4.0 g/day is reached, the patient being monitored daily for mercury in the urine and for the severity of side effects as described in connection with treatment of RA with sulfhydryls.

In the treatment of acute mercury poisoning the dosage is increased rapidly since life is threatened and toxic effects of long-term treatment with the sulfhydryl are of relatively little importance. Also, the treatment with sulfhydryl may be supplemented with hemodialysis since loss of kidney function within 24 to 36 hours is likely to occur.

Copper sulfhydryl complexes are also effective for the removal of several heavy metals though not of lead. For the copper sulfhydryl to be effective in removal of a heavy metal from the body, it is necessary that the heavy metal have an association constant for the sulfhydryl which is great enough to displace copper from the complex. In addition the heavy metal-sulfhydryl compound must be soluble in plasma. Mercuric ion, for instance reacts readily with copper penicillamine to displace the copper therefrom forming a soluble, colorless compound which can be excreted. Similarly, any other heavy metal ion which can displace the copper from the sulfhydryl complex to form a water-soluble product can be removed in the same way.

It is significant that copper cysteine which stabilizes the sulfhydryl in the form of a monomer is the safest medication for the purpose since it consists of cysteine which is a naturally occurring amino acid and copper, a naturally occurring element that is essential to life. Copper penicillamine is also of importance as a therapeutic compound since it it known that the body can tolerate the material in quantities great enough to be effective.

The dosage of the copper sulfhydryl to be used in the treatment of heavy metal poisoning is such as to correspond to a copper content of 2 to 15 mg of copper ranging from the minimal dietary intake of copper per day to about three times the maximal dietary intake per day. The daily dose is preferably administered in 2 to 3 portions. The patient is monitored with particular attention to the content of both copper and heavy metal in the urine. The actual dosage will be selected by the clinician on the basis of the patient's tolerance for the copper sulfhydryl combination, which may be a complex or a mixture. The mol ratio of the sulfhydryl to copper preferably lies between 1 and 5.

A point to be noted is that the molecular weights of the various sulfhydryls under consideration lie fairly close together. Accordingly, although the dosage in the treatment of RA, cystinuria and heavy metal poisoning may be adjusted in proportion to the molecular weight of the compound being administered in general, such adjustment is usually unnecessary, the response of the patient to the medication being the critical factor. However, where the sulfhydryl is trisubstituted, adjustment of the dosage in accordance with the molecular weight of the sulfhydryl is appropriate. Thus, methyl-cysteine has a molecular weight of 135.2 whereas α-chloro, β-chloro, β-hydroxyethyl cysteine has a molecular weight of 234.0. This point is illustrated in the next example.

EXAMPLE 9

A patient suffering from mercury poisoning is initially treated with 3 tablets/day of the reaction product of α-chloro, β-chloro, β-hydroxyethyl cysteine (I) with copper acetate in 3 divided doses, each tablet containing 23 mg of copper and 177 mg of I. The total daily dosage of copper amounts to 69 mg. The mol ratio of the sulfhydryl to cuprous ion is 2.0. The urine is examined daily for copper and mercury.

Since mercury poisoning is a life-threatening condition the dosage is increased each day by 1 tablet/day, monitoring the tolerance of the patient for the combination until a maximum of 10 tablets/day (230 mg of Cu/day) is reached, copper and mercury in the urine being monitored every day and the treatment being continued until the mercury content of the urine becomes negligible.

If α-methyl cysteine had been used instead of the trisubstituted cysteine then the comparable quantity of α-methyl cysteine in the tablet would have been 9.25 mg rather than 16 mg, thus illustrating compensation for the molecular weight of the substituted sulfhydryl.

In general, and especially when more than one dose is to be given per day, administration as a solid (in capsule or tablet form) is preferred to injection. However, intravenous injection is preferred where it is desired to maintain a high and essentially constant level of medication even at lengthy interval. For this purpose a solution of copper-penicillamine is particularly suitable because of the high aqueous solubility of the combination.

It will thus been seen that the objects set forth above among those made apparent from the preceding description, are efficiently attained and, since certain changes may be made in carrying out the above method without departing from the nature and scope of the invention, it is intended that all matter contained in the above description shall be interpreted as illustrative and not in a limiting sence.

It is also to be understood that the following claims are intended to cover all of the generic and specific features of the invention herein described, and all statements of the scope of the invention, which, as a matter of language, might be said to fall therebetween.

What is claimed is:

1. Method of treatment of rheumatoid arthritis comprising the step of administering to a patient with a rheumatoid arthritis treatment effective amount of a sulfhydryl compound selected from the group consisting of beta-monosubstituted cysteine, the substituent being selected from a first subgroup consisting of chloro, methyl, ethyl, hydroxymethyl and hydroxyethyl; beta-disubstituted cysteine, the substituents being selected from a second subgroup consisting of the pairs,

| | |
|---|---|
| chloro, | chloro, |
| methyl, | chloro, |
| ethyl, | chloro, |
| methyl, | ethyl, |
| ethyl, | ethyl, |
| hydroxymethyl, | hydroxymethyl, |
| hydroxyethyl, | hydroxylethyl, |
| hydroxymethyl, | hydroxyethyl, |
| methyl, | hydroxymethyl, |
| methyl, | hydroxyethyl, |
| ethyl, | hydroxymethyl, |
| ethyl, | hydroxyethyl, |
| chloro, | hydroxymethyl, and |
| chloro, | hydroxyethyl; | alpha-substituted cysteine, the substituent being selected from a third subgroup identical with said first subgroup;
 beta-monosubstituted, alpha-substituted cysteine, the substituents in both positions being selected from a fourth subgroup identical with the members of said first subgroup;
 alpha-substituted, beta-disubstituted cysteine, the substituents being selected from a fifth subgroup consisting of the combinations of the members of said first subgroup with the members of said second subgroup;
 an N-acetyl derivative of a member of said group of sulfhydryl compounds; and combinations of said compounds.

2. A method of treatment of rheumatoid arthritis, as defined in claim 1, wherein said sulfhydryl compound is β-methylcysteine.

3. A method of treatment of rheumatoid arthritis, as defined in claim 1, wherein said sulfhydryl compound is α-methylcysteine.

4. A method of treatment of rheumatoid arthritis, as defined in claim 1, wherein said sulfhydryl compound is α,β-dimethylcysteine.

5. A method of treatment of rheumatoid arthritis, as defined in claim 1, wherein said sulfhydryl compound is a metal complex with copper.

6. A method of treatment of rheumatoid arthritis, as claimed in any of claims 1 to 4 and 5, wherein said sulfhydryl compound is administered orally.

7. A method of treatment of rheumatoid arthritis, as claimed in any of claims 1 to 4 and 5, wherein said sulfhydryl compound is administered parenterally.

8. A method of treatment of rheumatoid arthritis, as claimed in claim 1, wherein said sulfhydryl compound is cysteine complexed with copper.

9. A method of treatment of rheumatoid arthritis, as defined in claim 1, wherein said sulfhydryl compound is β-methylcysteine complexed with copper.

10. A method of treatment of rheumatoid arthritis, as claimed in claim 5, wherein the mol ratio of said sulfhydryl to the copper in said source of copper lies in the range from about 1 to 5.

11. A method of treatment of rheumatoid arthritis comprising the step of administering to a patient with rheumatoid arthritis, a rheumatoid arthritis treatment effective amount of a complex of a sulfhydryl of the group of sulfhydryls consisting of cysteine, α-methylcysteine and β-methylcysteine, complexed with copper said complex being water-soluble.

12. A composition effective in the treatment of rheumatoid arthritis, comprising a water-soluble complex of at least one sulfhydryl compound selected from the groups consisting of cysteine, beta-monosubstituted cysteine, the substituent being selected from a first subgroup consisting of chloro, methyl, ethyl, hydroxymethyl and hydroxyethyl; beta-disubstituted cysteine, the substituents being selected from a second subgroup consisting of the pairs,

| | |
|---|---|
| chloro, | chloro, |
| methyl, | chloro, |
| ethyl, | chloro, |
| methyl, | ethyl, |
| ethyl, | ethyl, |
| hydroxymethyl, | hydroxymethyl, |
| hydroxyethyl, | hydroxylethyl, |
| hydroxymethyl, | hydroxyethyl, |
| methyl, | hydroxymethyl, |
| methyl, | hydroxyethyl, |
| ethyl, | hydroxymethyl, |
| ethyl, | hydroxyethyl, |
| chloro, | hydroxymethyl, and |
| chloro, | hydroxyethyl; | alpha-substituted cysteine, the substituent being selected from a third subgroup identical with said first subgroup;
 beta-monosubstituted, alpha-substituted cysteine, the substituents in both positions being selected from a fourth subgroup identical with the members of said first subgroup;
 alpha-substituted, beta-disubstituted cysteine, the substituents being selected from a fifth subgroup consisting of the combinations of the members of said first subgroup with the members of said second subgroup; and
 an N-acetyl derivative of a member of said group of sulfhydryl compounds; and combinations of said compounds; complexed with copper.

13. A composition as claimed in claim 12 wherein said complex is the reaction product of said compound of said group of said compound of copper.

14. A composition as claimed in claim 13 wherein said reaction product is a member of the group consisting of copper-cysteine, copper α-methylcysteine, copper β-methylcysteine and copper α,β-dimethylcysteine.

15. A composition effective in the treatment of rheumatoid arthritis, comprising a water-soluble complex of at least one sulfhydryl compound selected from the groups consisting of cysteine, beta-monosubstituted cysteine, the substituent being selected from a first subgroup consisting of chloro, methyl, ethyl, hydroxymethyl and hydroxyethyl; beta-disubstituted cysteine, the substituents being selected from a second subgroup consisting of the pairs,

| | |
|---|---|
| chloro, | chloro, |
| methyl, | chloro, |
| ethyl, | chloro, |
| methyl, | ethyl, |
| ethyl, | ethyl, |
| hydroxymethyl, | hydroxymethyl, |
| hydroxyethyl, | hydroxylethyl, |
| hydroxymethyl, | hydroxyethyl, |
| methyl, | hydroxymethyl, |
| methyl, | hydroxyethyl, |
| ethyl, | hydroxymethyl, |
| ethyl, | hydroxyethyl, |

| -continued | |
|---|---|
| chloro, | hydroxymethyl, and |
| chloro, | hydroxyethyl; | alpha-substituted cysteine, the substituent being selected from a third subgroup identical with said first subgroup;

beta-monosubstituted, alpha-substituted cysteine, the substituents in both positions being selected from a fourth subgroup identical with the members of said first subgroup;

alpha-substituted, beta-disubstituted cysteine, the substituents being selected from a fifth subgroup consisting of the combinations of the members of said first subgroup with the members of said second subgroup; and an N-acetyl derivative of a member of said group of sulfhydryl compounds; and combinations of said compounds;

complexed with copper, wherein the mole ratio of the sulfhydryl compound to the copper is in the range from about 1 to 5.

16. A composition effective in the treatment of rheumatoid arthritis, comprising a water-soluble complex of at least one sulfhydryl compound selected from the group consisting of copper-cysteine, copper alpha-methyl cysteine, copper beta-methyl cysteine and copper alpha-beta-dimethyl cysteine.

* * * * *